(12) United States Patent
Bratov et al.

(10) Patent No.: US 8,608,919 B2
(45) Date of Patent: Dec. 17, 2013

(54) IMPEDIMETRIC SENSOR AND APPLICATIONS THEREOF

(75) Inventors: Andrei Bratov, Bellaterra (ES); Carlos Domínguez Horna, Bellaterra (ES); Natalia Abramova, Bellaterra (ES); Ángel Merlos Domingo, Bellaterra (ES); Javier Ramon Azcon, Barcelona (ES); Francisco José Sanchez Baeza, Barcelona (ES); María Pilar Marco Colas, Barcelona (ES)

(73) Assignee: Consejo Superior de Investigaciones Científicas, Madrid (ES)

( * ) Notice: Subject to any disclaimer, the term of this patent is extended or adjusted under 35 U.S.C. 154(b) by 833 days.

(21) Appl. No.: 12/599,378

(22) PCT Filed: Apr. 29, 2008

(86) PCT No.: PCT/ES2008/070084
§ 371 (c)(1),
(2), (4) Date: Dec. 21, 2009

(87) PCT Pub. No.: WO2008/139016
PCT Pub. Date: Nov. 20, 2008

(65) Prior Publication Data
US 2010/0193378 A1    Aug. 5, 2010

(30) Foreign Application Priority Data

May 9, 2007  (ES) .................................. 200701253

(51) Int. Cl.
*G01N 27/327*  (2006.01)
*G01N 27/416*  (2006.01)

(52) U.S. Cl.
USPC .. 204/403.01; 205/779; 205/792; 204/403.02

(58) Field of Classification Search
USPC .............. 204/403.01–403.06, 403.1–403.15;
205/777.5–778, 792, 793;
600/345–348
See application file for complete search history.

(56) References Cited

U.S. PATENT DOCUMENTS

| 5,846,708 A | 12/1998 | Hollis et al. |
| 6,440,662 B1 | 8/2002 | Gerwen |
| 2002/0150886 A1 | 10/2002 | Miles |
| 2003/0042150 A1* | 3/2003 | Ryu et al. .................... 205/778 |
| 2004/0023253 A1* | 2/2004 | Kunwar et al. ................ 435/6 |

(Continued)

FOREIGN PATENT DOCUMENTS

| EP | 0241771 | 10/1987 |
| EP | 0543550 | 5/1993 |

(Continued)

OTHER PUBLICATIONS

Bataillard, P. et al., Analytical Chemistry, 1988, 60, 2374-2379.

(Continued)

*Primary Examiner* — Susan D Leong
(74) *Attorney, Agent, or Firm* — Merchant & Gould P.C.

(57) ABSTRACT

A highly sensitive impedimetric sensor in which the highly conductive electrodes are separated by a barrier of insulating material is disclosed. The sensor is used to determine directly the presence of analytes in a biological sample of human, veterinary or environmental origin.

16 Claims, 5 Drawing Sheets

(56) References Cited

U.S. PATENT DOCUMENTS

| | | |
|---|---|---|
| 2004/0110277 A1 | 6/2004 | Maeda |
| 2005/0084865 A1* | 4/2005 | Yu et al. ............................ 435/6 |
| 2005/0142033 A1* | 6/2005 | Glezer et al. .................... 422/58 |
| 2005/0176067 A1 | 8/2005 | Fleischer |
| 2005/0247559 A1 | 11/2005 | Frey et al. |
| 2006/0037859 A1* | 2/2006 | Hodges et al. ................ 204/400 |

FOREIGN PATENT DOCUMENTS

| | | |
|---|---|---|
| EP | 1607739 A1 | 12/2005 |
| GB | 2137361 | 10/1984 |
| JP | 2003-185662 | 7/2003 |
| JP | 2005-536718 | 12/2005 |
| WO | WO 03/087798 | 10/2003 |
| WO | 2004044570 | 5/2004 |
| WO | 2004065624 | 8/2004 |
| WO | 2005001479 | 1/2005 |
| WO | 2005026178 | 3/2005 |
| WO | 2007042356 A1 | 4/2007 |

OTHER PUBLICATIONS

Berggren, et al., Electroanalysis, 2001, 13, 173-180.

Dharuman, et al., Label-free impedance detection of oligonucleotide hybridisation on interdigitated ultramicroelectrodes using electrochemical redox probes, Biosensors & Bioelectronics, 21, 2005, 645-654.

Elsholz, et al. Automated detection and quantitation of bacterial RNA by using electrical microarrays, Analytical Chemistry, 78 (14): 4794-4802, Jul. 15, 2006.

Honda, et al. High efficiency electrochemical immuno sensors using 3D comb electrodes, Biosensors & Bioelectronics, 20 (11): 2306-2309, May 15, 2005.

Laureyn, et al., Sensors and Actuators B, 2000, 68, 360-370.

Li XH, et al., HB Electrochemical detection of single-nucleotide mismatches using an electrode microarray Analytical Chemistry, 78 (17): 6096-6101, Sep. 1, 2006.

Schoning, M.J. & Poghossian, A. "Recent advances 1-14 in biologically sensitive field-effect transistors (BioFETs)". The Analyst, 2002, vol. 127, pp. 1137-1151.

Shi MH, et al., Immunoassays based on microelectrodes arrayed on a silicon chip for high throughput screening of liver fibrosis markers in human serum Biosensors & Bioelectronics, 21 (12): 2210-2216, Jun. 15, 2006.

Van Gerwen, et al, Sensors and Actuators B, 1998, 49:73-80.

Wang JB, et al., Au nanoparticle conjugation for impedance and capacitance signal amplification in biosensors, Analytical Chemistry, 78 (6): 1769-1773, Mar. 15, 2006.

\* cited by examiner

IMPEDIMETRIC SENSOR AND APPLICATIONS THEREOF

This application is a National Stage Application of PCT/ES2008/070084, filed 29 Apr. 2008, which claims benefit of Serial No. P200701253, filed 9 May 2007 in Spain and which application(s) are incorporated herein by reference. To the extent appropriate, a claim of priority is made to each of the above disclosed applications.

TECHNICAL SECTOR

The present invention is framed within the field of impedimetric biosensors suitable for directly monitoring biochemical reactions which involve receptor molecules which are directly connected to the surface of the sensor and, in particular, to the surface of an insulating barrier which separates two highly conductive electrodes.

STATE OF THE ART

Figure 1:
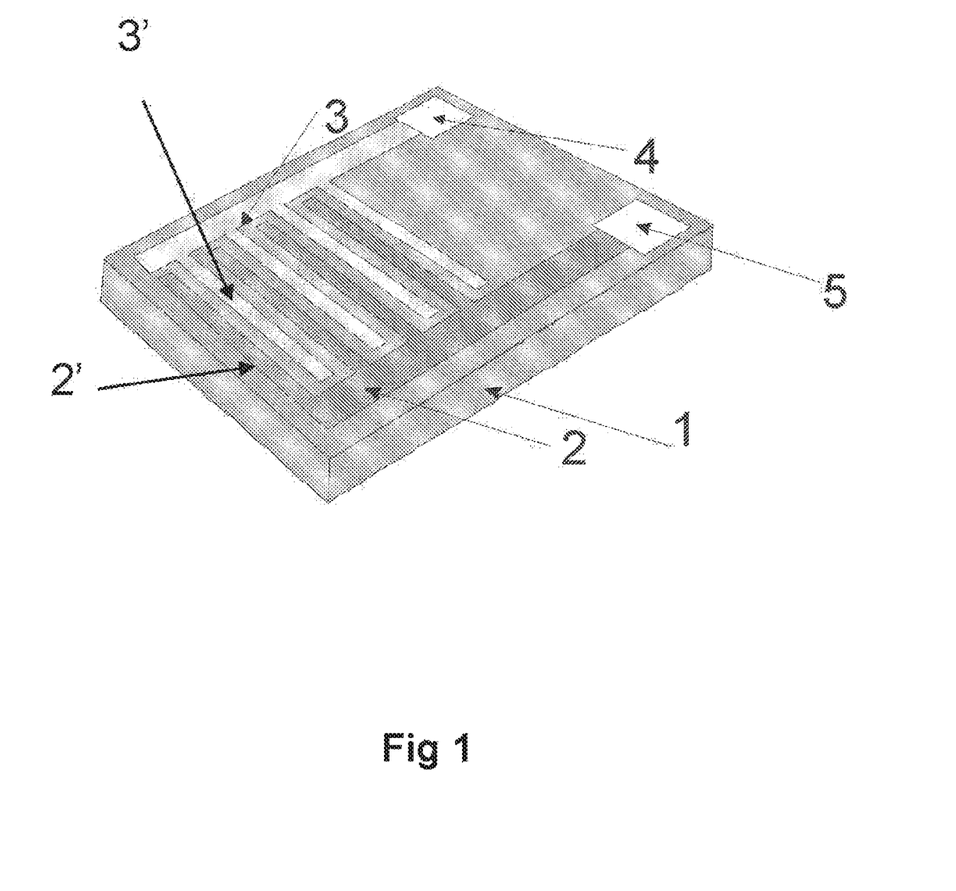
FIG. 1—Traditional impedimetric transducer with two coplanar interdigitated electrodes, called Interdigitated Electrode Array (IDEA). This transducer is constituted by an insulating substrate (1), two collector bars (2) and (3) which connect the "digitated" electrodes (2' and 3') and the welding points (4) and (5).

It is known that the measurements of impedance are used to record the biochemical reactions which take place on the surface of chemically modified electrodes, in the case of immunological reactions (Bataillard, P. et al., Analytical Chemistry, 1988, 60, 2374-2379; C. Berggren, B. Bjarnanson, G. Johansson, Electroanalysis 2001, 13, 173); as well as for the direct measurement of the hybridisation of DNA (Patent WO2004065624; Li X H, Lee J S, Kraatz H B Electrochemical detection of single-nucleotide mismatches using an electrode microarray ANALYTICAL CHEMISTRY 78 (17): 6096-6101 Sep. 1 2006). With the aim of increasing the sensitivity of the measurements and miniaturizing the sensor element, an impedimetric transducer formed by two flat electrodes with interdigitated geometry, called Interdigitated Electrode Array (P. Van Gerwen, et al, Sens. Actuat. B 1998, 49, 73; W. Laureyn, et al., Sens. Actuat. B 2000, 68, 360) (Interdigitated Electrode Array, IDEA). In FIG. 1, an orthogonal projection of the transducer is represented, which comprises an insulating substrate (1), two collector bars (2) and (3) which connect the digitated electrodes to the welding contacts (4) and (5).

The central idea of the impedimetric measurement has previously been dealt with in several patents (WO2004044570, EP 0543550, EP 0241771, GB 2,137,361). Essentially, in an impedimetric sensor, such as the one represented in FIG. 2, certain molecules are immobilised either on the surface of the electrode, between each pair of digitated electrodes, or on the surface between a pair of digits. These molecules "recognize" a specific analyte when they are exposed in a sample solution. The recognition process generally ends in a variation of the conductivity and/or permittivity of the medium which surrounds the electrodes. These variations are recorded as changes in the impedance spectrum, measured in a wide range of frequencies. Finally, by measuring the impedance between the two electrodes, one can be establish the magnitude of the recognition process by means of adjusting the parameters of an equivalent electrical circuit, which is removed from the shape of the spectrum and is shown schematically in FIG. 2.

The physical significance of the elements which form the equivalent circuit is as follows: $R_C$—contact resistance of the connection threads, contacts and collector bars; $C_G$—geometrical capacity established between two electrodes and the contact medium (typically an aqueous solution); $R_S$—electrical resistance of the aqueous solution between two electrodes; $C_{DL}$—double layer capacity on the interphase electrode/solution; $R_{CT}$—resistance to the charge transfer due to the Faraday processes on the surface of the electrode; W—additional polarization in the concentration (Warburg impedance), roughness of the surface of the electrodes and/or presence of an additional layer on the surface of the electrodes.

The problem presented by sensors with immobilised sensors on the electrodes, as has been previously described, is that in order to obtain a measurement with a good resolution and sensitivity, it is necessary for the immobilised layer on the conductor electrodes (6, in FIG. 2B) to be perfectly homogeneous and continuous, which is difficult to achieve.

Figure 2A:
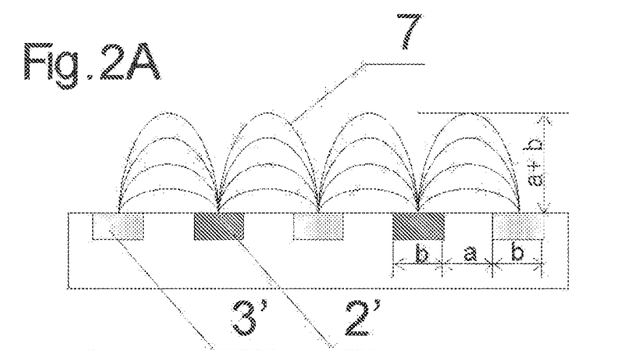
Figure 2B:
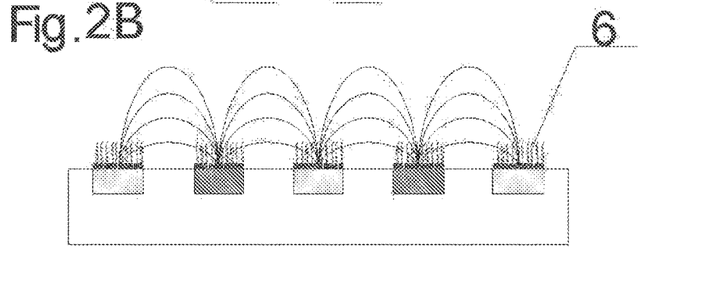

The parameters of the impedimetric sensor, described above, depend on the geometry of the digitated electrodes; i.e., on the width of each digit and on the separation between digits (parameters a and b from FIG. 2A). The larger part of the signal is due to a region on the electrodes whose penetration in the medium is equal to the distance between the centres of two adjacent digitated electrodes, as described in FIG. 2A, where the vector lines (7) are shown schematically. The typical length of the biomolecules is in the range of between 10-100 nm, which implies that for the case in which the molecules are immobilised in the space between each pair of digitated electrodes, the size of the digits and the separation between them have to be very small, which is difficult to achieve with conventional microelectronic technology.

Due to the difficulties stated above, these sensors, when one tries to use them in direct measurements, have a lesser sensibility than other conventional methods.

As claimed in patents: WO2005026178, US2005176067, in order to increase the sensitivity of the interdigitated electrode arrays, indirect analyses have been used for immuno-(Shi M H, Peng Y Y, Zhou J, et al. Immunoassays based on microelectrodes arrayed on a silicon chip for high throughput screening of liver fibrosis markers in human serum BIOSENSORS & BIOELECTRONICS 21 (12): 2210-2216 Jun. 15 2006), DNA (V. Dharuman, et al., Label-free impedance detection of oligonucleotide hybridisation on interdigitated ultramicroelectrodes using electrochemical redox probes, Biosensors & Bioelectronics 21 (2005) pp. 645-654) or RNA (Elsholz B, Worl R, Blohm L, et al. Automated detection and quantitation of bacterial RNA by using electrical microarrays ANALYTICAL CHEMISTRY 78 (14): 4794-4802 Jul. 15 2006), based on the production or registration of redox species. In order to increase the electrochemical sensitivity of these sensors, the use of three-dimensional interdigitated electrodes has been proposed, which contain 30 μm thick metal electrodes (Honda N, Inaba M, Katagiri T, et al. High efficiency electrochemical immuno sensors using 3D comb electrodes BIOSENSORS & BIOELECTRONICS 20 (11): 2306-2309 May 15 2005).

Another way to improve the sensitivity of the impedimetric sensitivity consists of using metallic or polymeric particles bonded to the molecule which is to be detected (Wang J B, Profitt J A, Pugia M J, et al. Au nanoparticle conjugation for impedance and capacitance signal amplification in biosensors ANALYTICAL CHEMISTRY 78 (6): 1769-1773 Mar. 15 2006), as disclosed in patents US2002150886, WO2005001479. The interaction between the marked molecules and the immobilised receptors on the sensor results in the production of a greater interference with the electrical field and, consequently, a greater sensitivity.

In U.S. Pat. No. 6,440,662, a three-dimensional IDEA sensor is presented, formed from partially covered channels with a metal sheet and which, together with a metallic surface layer, make up the sensor electrodes. This geometry permits a redistribution of the analysed electrical field and an increase of the sensitivity of the sensor.

DESCRIPTION OF THE INVENTION

Brief Description

Figure 4A:
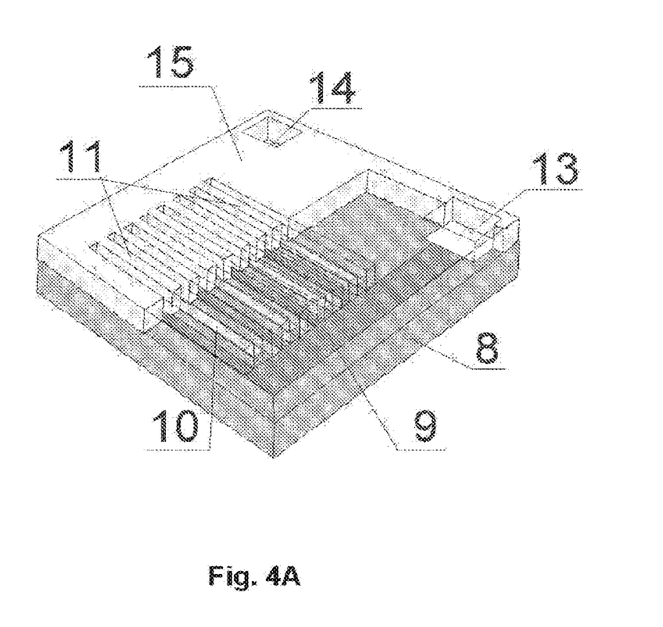
FIG. 4—(A) The impedimetric sensor comprises: a substrate (8) coated by an insulating layer whereon are found the pairs of interdigitated electrodes (9) and (10), made of a very good electrically conductive material, and separated by a dielectric barrier (11), whose height is equal to the distance between the centres of two electrode digits. The material which forms the barriers between digits is a good insulator (15) whereon the welding points (14 and 15) open. (B) Cross-sectional view of the device featured in FIG. 4A, where the substrate (8), the electrodes (9 and 10), the barrier (11) which separates them and the vectors of the electrical field (7) are shown. (C) Sectional view of the device shown in FIG. 4A which includes the layer of receptor molecules (12) immobilised on the surface of the barriers.

One object of the present invention is constituted by a useful biosensor, hereinafter biosensor of the invention, for directly determining the presence of analytes in a sample, which comprises (FIG. 4):

i) an insulating substrate (8) or cover with an insulating layer, ii) at least, a pair of chemically inert interdigitated electrodes ((9) and (10)) formed with a highly conductive electrical material, disposed on the substrate and each pair of digits separated by iii) a barrier (11) made of an insulating material, whose height is similar to the distance existing between the centres of the pair of adjacent digitated electrodes, into which the welding points (13 and 14) open, and iv) chemically immobilised receptor molecules (12) on the surface of the insulating material or on the surface of the electrodes.

One specific object of the invention is constituted by the biosensor of the invention in which the insulating substrate from i) is of a material belonging, illustratively and without this limiting the scope of the invention, to the following group: a polymer, a glass or an inorganic oxide.

Another specific object of the invention is constituted by the biosensor of the invention in which the substrate from i) is not of an insulating material but rather comprises an insulating or dielectric layer of a material belonging, illustratively and without this limiting the scope of the invention, to the following group: silicon dioxide or a polymer.

Another specific object of the invention is constituted by the biosensor of the invention in which the highly conductive and inert electrodes from ii) are of a material belonging, illustratively and without this limiting the scope of the invention, to the following group: metals, preferably Pt, Pd and Au, oxides, Si, silicon polycrystalline, tantalum silicide or, even, polymer conductors.

Another specific object of the present invention is constituted by the biosensor of the invention in which the electrodes have digits with a width and a separation between them between the ranges of 0.5 to 10.0 μm.

Another specific object of the present invention is constituted by the biosensor of the invention in which the insulating barrier from iii) is of a material belonging, illustratively and without this limiting the scope of the invention, to the following group: inorganic oxides, polymers and materials sensitive to the exposure of UV light.

Another specific object of the invention is constituted by the biosensor of the invention in which the insulating barrier from iii) features a thickness of the insulating layer, which defines the height of the barrier which separates two adjacent digits, which means that it is between 50% and 150% of the distance which separates the centres of a pair of consecutive digitated electrodes, or more preferably, close to 100%.

Another specific object of the present invention is constituted by the biosensor of the invention which further comprises a device or apparatus which detects the electrical properties connected to the electrodes from ii) whereto is applied an AC voltage, and which detects the variation in the electrical field close to the surface of the barriers, and a device or apparatus to apply said voltage.

Another specific object of the present invention is constituted by the use of the biosensor of the invention, hereinafter use of the biosensor of analytes or molecules which are found in a biological sample.

DETAILED DESCRIPTION

One objective of the present invention is that of providing a new electrochemical biosensor and a method capable of determining the presence or absence of molecular structures or analytes in a problem sample.

The present invention is based on the fact that the inventors have observed that they can build a new highly sensitive electrochemical sensor whose operational principle is based on the interference which is produced between an electrical field generated between two electrodes and the molecular structures which can be formed due to the interaction of analytes from a sample in solution with the receptor molecules or immobilised sensors on the surface of the sensor, and in which the highly conductive electrodes are separated by a barrier of an insulating material (see Examples 1 to 3).

The biochemical reactions which take place in said molecular interaction affect the distribution of ionic charges and, therefore, the electrical properties of the layers close to the surface of the barrier. An AC voltage is applied to the electrodes through a detection device whereto they are connected, detecting the impedance changes which are produced between them. Due to the presence of the insulating barrier, most of the current which flows between the electrodes passes through a thin layer very close to the surface of the barrier, which permits the increase of the sensitivity to the impedance changes derived from the biochemical processes.

Figure 2C:
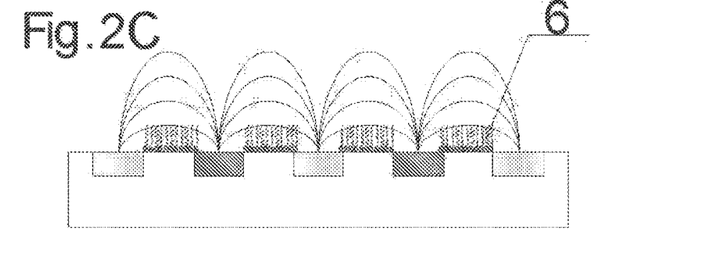
Figure 4B:
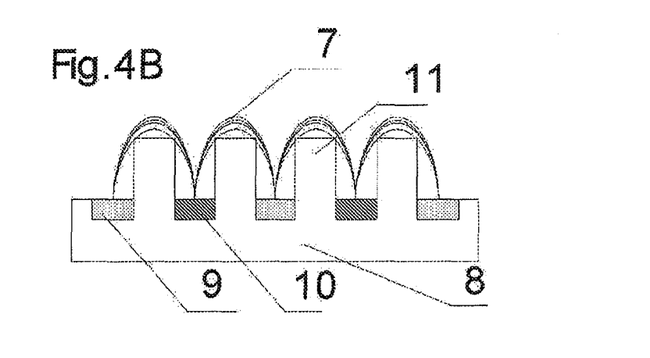
Figure 4C:
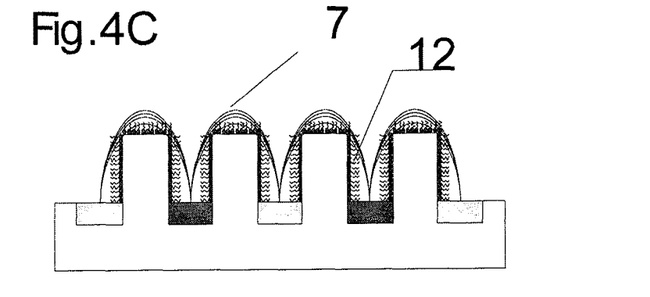
Figure 5:
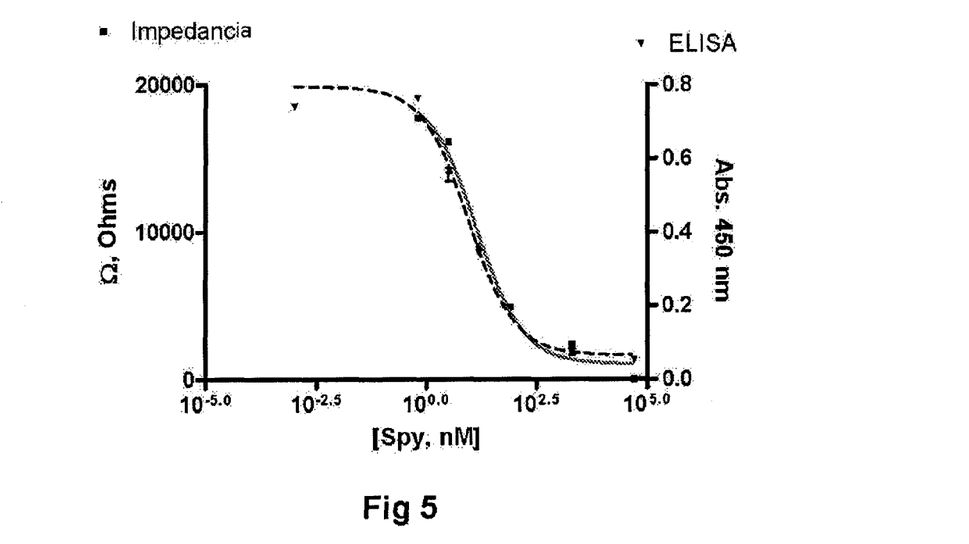
FIG. 5—Calibration curve for the ELISA immunoassay (dotted line) and the immunosensor of the invention (continuous red line) against the sulfapyridine solution.
Figure 6:
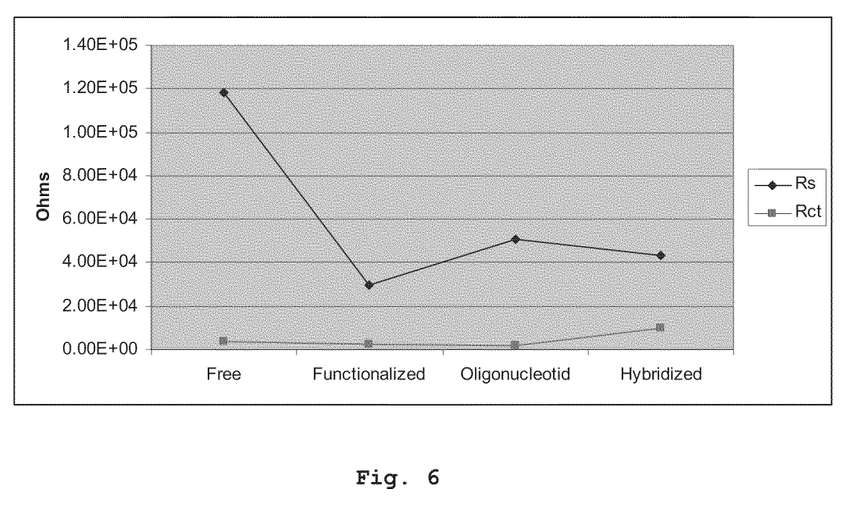
FIG. 6—Parameters $R_S$ y $R_{CT}$ produced from the equivalent circuit shown in FIG. 3, by means of adjusting the impedance spectrum measured at different times of the experiment.

More specifically, if an electrical signal is applied, whether it is a difference of voltage or a current, in the welding points (13) and (14) of the sensor of the invention (FIG. 4A), an electrical field appears which leads to a series of vector lines (7) (FIG. 4B). If the molecules or analytes which have to be detected are found in the sample solution, then they will bond to the receptor molecules or sensors (12) producing a strong variation in the electrical field close to the surface of the barriers, variation which in the arrangement of FIG. 2C is much less. This variation can be quantified by measuring the impedance at a frequency and/or a suitable DC polarization (see Examples 2 and 3).

Therefore, an object of the present invention is constituted by a useful biosensor to directly determine the presence of analytes in a sample, hereinafter biosensor of the invention, which comprises (FIG. 4):

i) an insulating substrate (8) or cover with an insulating layer, ii) at least, a pair of chemically inert interdigitated electrodes ((9) and (10)) formed with a highly conductive electrical material, disposed on the substrate and each pair of digits separated by iii) a barrier (11) made of an insulating material, whose height is similar to the distance existing between the centres of the pair of adjacent digitated electrodes, into which the welding points (13 and 14) open, and iv) chemically immobilised receptor molecules (12) on the surface of the insulating material or on the surface of the electrodes.

Receptor molecules in this invention are understood to be those operationally defined molecules which are capable of reacting or bonding to other molecules or analytes of a sample to form a complex and/or induce a secondary reaction. As an example, the receptor molecules can be enzymes, antibodies, antigens, peptides, DNA fragments, RNA fragments or oligonucleotides.

The analytes or molecules to be determined in a solution or a sample can be any molecule present in the sample which bonds to or reacts with the receptor molecules. The analytes to be determined can be, illustratively and without limiting the scope of the invention, enzymes, antibodies, antigens, peptides, DNA fragments, RNA fragments, oligonucleotides or even complete cells of different types such as eukaryotes or prokaryotes.

The bond between a receptor molecule and an analyte takes place, for example, in hybridisations of single DNA and/or RNA chains, antigen/antibody and enzyme/substrate reactions, within problem analyte identification procedures within a sample, preferably biological, of clinical or veterinarian, alimentary or environmental origin, amongst others.

The substrate from i), called base layer, can be of different types of materials, for example a crystalline wafer (quartz, silicon, sapphire), an amorphous material (glass), a polymer (PMMA, PCC, PEEK, PVE, PEI) or a thick layer of ceramic material, such as $Al_2O_3$. In the event that the substrate is not insulating, an insulating dielectric layer must be formed on the surface thereof. This insulating layer can be a polymeric layer, such as a polyimide or a BCB, or an inorganic material, for example $Si_3N_4$ deposited by LPCVD or PECVD techniques, or a layer of $SiO_2$ deposited or grown thermally on a silicon wafer.

One specific object of the invention is constituted by the biosensor of the invention in which the insulating substrate from i) is of a material belonging, illustratively and without this limiting the scope of the invention, to the following group: a polymer, a glass or an inorganic oxide.

Another specific object of the invention is constituted by the biosensor of the invention in which the substrate from i) is not of an insulating material but rather comprises an insulating or dielectric layer of a material belonging, illustratively and without this limiting the scope of the invention, to the following group: silicon dioxide or a polymer.

The electrodes from ii) are formed by a layer of a good electrical conducting material, deposited on the dielectric layer, preferably using evaporation techniques. The geometry of the electrodes is defined by means of lithographic techniques, followed by direct etching techniques or by lift-off. The width and separation between each pair of digitated electrodes (parameters a and b in FIG. 1A) must be of sizes which are preferably in the micrometric range; nevertheless, they can also be in the sub-micrometric range. Any material which is a good electrical conductor and which does not react with the solution can be used to form the electrodes. Illustratively and without limiting the scope of the invention, can be used: Pt, Pd, Au or materials such as Si, silicon polycrystalline, tantalum silicide or even polymer conductors, as long as reactions which alter the integrity of the electrodes do not take place. The thickness of the conductive layer can be very wide, but for the application as biochemical sensor a thickness of around 150 nm is recommended. The deposition of the layer can be achieved by means of thermal evaporation, cathode sputtering, electron gun or any other known technique which permits the production of layers of electrically conductive materials, and is within the scope of a person skilled in the art.

Another specific object of the invention is constituted by the biosensor of the invention in which the highly conductive and inert electrodes from ii) are of a material belonging, illustratively and without this limiting the scope of the invention, to the following group: metals, preferably Pt, Pd and Au, oxides, Si, silicon polycrystalline, tantalum silicide or, even, polymer conductors.

Another specific object of the present invention is constituted by the biosensor of the invention in which the electrodes have digits with a width and a separation between them between the ranges of 0.5 to 10.0 μm.

In order to obtain a reliable connection between the impedimetric sensor and the external measurement circuit, for example an impedance meter, it is necessary to make welding points (13) and (14), continuing with the manufacturing process as commented below. A metallic layer is deposited on the surface of the sensor whose structural pattern is defined, using contrast masks and photolithographic processes and conventional etching. The metal of the welding point can be of any metal which guarantees a good threaded weld and a low contact resistance with the underlying material, which makes up the conductive electrodes. This metal, as an example, can be aluminium.

The dielectric barriers between each pair of adjacent electrodes of the interdigitated structure are created by means of depositing a layer of insulating material (15) which is eliminated on top of the metallic electrodes (digits) and of the welding points by means of using the photolithographic UV processes and etching, mainly deep reactive ion etching (DRIE). The thickness of the insulating layer, which defines the height of the barrier which separates two adjacent digits, is supposedly equal to 100% of the distance which separates the centres of said pair of adjacent digitated electrodes. Likewise, it is possible to have barriers with heights which vary from between 50% and 150% of the intercentral distance of two consecutive digits, or with thicknesses above or below this range. Except for in the collector barriers (2, in FIG. 1), where it is essential to prevent contact thereof with the solution to be analysed; within the scope of this invention, it is not critical to keep the insulating layer on other parts of the surface of the sensor. The dielectric material used to form the barriers can be any type of insulating material, although due to technological reasons it is preferable to use as such the silicon dioxide obtained via LPCVD, since it can be easily eliminated. The shape of the barriers produced after the etching process is also not critical, as these can be rectangular, with sloped or vertical walls, and flat or round in the upper part.

Besides that described and according to the state of the art, other methods can be used within the scope of the present invention in order for a person skilled in the art to produce the barriers which separate the different electrodes. Thus, materials sensitive to being exposed to UV light could be used to define the barriers; micro-moulding techniques can also be used, such as capillary Micromolding, Replica Molding, Micromolding assisted by solvents, etc.

Another specific object of the present invention is constituted by the biosensor of the invention in which the insulating barrier from iii) is of a material belonging, illustratively and without this limiting the scope of the invention, to the following group: inorganic oxides, polymers and materials sensitive to the exposure of UV light.

Another specific object of the present invention is constituted by the biosensor of the invention in which the insulating barrier from iii) features a thickness of the insulating layer, which defines the height of the barrier which separates two adjacent digits, which means that it is between 50% and 150% of the distance which separates the centres of a pair of consecutive digitated electrodes, or more preferably, close to 100%.

The receptor molecules from iv) (12, FIG. 4) can be immobilised on the surface of the insulating barrier in accordance with the molecule immobilisation methods known in the state of the art, in the way of illustration and without limiting the scope of the invention: bonding by epoxide, carbodiimide, reduction refining, cyanogen bromide, succinimide, carbodiimidazol, tresyl and tosyl chloride, divinyl chloride, maleimide, hydrazide, iso(thio)cyanate and, preferably, by silinasation with amino silanes, epoxide silanes, thiocyanate and isothiocyanate silanes, succinic anhydride silanes, sulfhydryl silanes and caprolactam silanes.

The receptor molecules consist of biological molecules which are capable of bonding to their corresponding analyte present in the biological sample to be analysed. Another alternative form of the sensor of the invention is that wherein the receptor molecules from iv) are immobilised on the surface of the electrodes.

The described technological process permits, by means of the use of conventional microelectronic technology, a great miniaturization of the sensors and, also, the construction of arrays of these built-in sensors on a single substrate. The built-in sensor arrays manufactured following the described methodology permit the production of devices for microdiagnostics. These built-in devices are capable of simultaneously detecting a multitude of parameters, this is multiparametric analysis. That has particular importance in situations where the sample is small and when one wants to carry out screening assays.

Another specific object of the present invention is constituted by the biosensor of the invention wherein the electrodes are organized according to an interdigitated array.

The variation of the electrical field of the biosensor upon producing the bond between the receptor molecule and the analyte can be quantified by measuring the impedance at a suitable frequency and/or DC polarization. The impedance analysis is the preferred electrical measurement, as this analysis can bring reveal the measurement of the resistance, capacity, dielectric and/or reactance loss, on a range of frequencies, including or not the DC polarization, or a combination of both techniques.

Another specific object of the present invention is constituted by the biosensor of the invention which further comprises a device or apparatus which detects the electrical properties connected to the electrodes from iii) whereto is applied an AC voltage, and which detects the variation in the electrical field close to the surface of the barriers, and a device or apparatus to apply said voltage.

Another specific embodiment is constituted by the biosensor of the invention wherein the detection device is an impedimeter which measures the impedance between the electrodes of the sensor.

Another specific embodiment is constituted by the biosensor of the invention which comprises several biomolecular sensors, whether, because they are of different type of biomolecules, for example, a nucleic acid (for example, a probe or an oligonucleotide), antigens, antibodies, enzymes, proteins or peptides, or because being of the same type of molecule they head towards one or more different target molecules.

Another specific object of the present invention is constituted by the use of the biosensor of the invention, hereinafter use of the biosensor of analytes or molecules which are found in a biological sample.

As has been previously commented, the analytes to be determined can be, illustratively and without limiting the scope of the invention, enzymes, antibodies, antigens, peptides, DNA fragments, RNA fragments, oligonucleotides or, even, complete cells of different types such as eukaryotes or prokaryotes and their identification may be of interest for example in the field of diagnostics of human or veterinary illnesses, environmental analyses, forensic analyses, etc.

DESCRIPTION OF THE FIGURES

FIG. 2—Cross-section of the transducer schematized in FIG. 1. (A) The interdigitated electrodes (2') and (3') are shown, with a width equal to "b" and a distance between electrodes equal to "a", and the vectors of the electrical field (7). The greater density of electrical field is enclosed in a region within a distance equal to the distance between centres of two adjacent electrodes (a+b) disposed on the surface of the device. (B) Example showing receptor molecules (6) immobilised on the digital electrodes. (C) Example showing immobilised molecules (6) between the digital electrodes.

FIG. 3—Electrical circuit equivalent to an interdigitated electrode array. The physical significance of the elements which form the equivalent circuit is as follows: $R_C$—contact resistance of the connection threads, contacts and collector bars; $C_G$—geometrical capacity established between two electrodes and the contact medium (typically an aqueous solution); $R_S$—electrical resistance of the aqueous solution between two electrodes; $C_{DL}$—double layer capacity on the interphase electrode/solution; $R_{CT}$—resistance to the charge transfer due to the Faraday processes on the surface of the electrode; W—additional polarization in the concentration (Warburg impedance), roughness of the surface of the electrodes and/or presence of an additional layer on the surface of the electrodes.

EXAMPLES OF EMBODIMENT OF THE INVENTION

Example 1

Manufacture of the Impedimetric Sensor of the Invention

The starting material for this specific embodiment of the invention was a silicon wafer. Given that it is only going to be used as a substrate, neither the type nor the dose of the drug is important, nor is the conductivity value or the crystalline orientation. The silicon wafer was thermally oxidized, at 950° C. in a wet oxidation process, forming a layer of 2500 nm of silicon dioxide of good dielectric quality. The next step consisted of depositing a layer of tantalum silicide, highly conductive, of 230 nm in thickness by means of cathode sputtering by magnetron.

The first photolithographic level defined the collector bars and the digits of the two electrodes. The definition of the motives was made with the reactive ion etching techniques. As a result, an array with 216 digits was produced, each one 3.0 μm thick and others with 3.0 μm of distance between adjacent digits. The aperture between the electrodes was of 1.4 mm, and their total length was 301.0 mm for each electrode.

The welding points were formed by depositing a layer of 1.0 μm of aluminium, and were disposed, by means of using conventional photolithographic and etching techniques, at the ends of the collector bars.

The final step was producing the insulating barriers. To do this, the surface of the wafer was covered with a layer of, in this case, 4.0 μm of silicon oxide deposited by LPCVD. Photolithography and etching was once again used to create the pattern which permitted leaving the material between the digits and cover the collector bars, except at the welding points. The elimination of this layer was performed with the deep reactive ion etching (DRIE) technique, which provides barriers with almost vertical walls. The height of the barrier was, in this specific case, almost 67% of the distance between two adjacent digits.

Once the wafer was cut, the individual devices were stuck to a PCB substrate and the threads were welded for the electrical connection with an impedimeter.

Example 2

Use of the Sensor of the Invention as Immunosensor

Before proceeding to the functionalization, the electrodes were cleaned in a solution of 70% absolute ethanol and 30% Milli-Q water. Afterwards, the devices were submerged in a solution of 2.5% NaOH and Milli-Q water for 10 minutes, followed by a rinsing in 100 mL of Milli-Q water, in order to neutralize the action of the NaOH. Finally, the electrodes were cleaned in ethanol and dried in nitrogen current.

The electrodes were introduced into a GPTS [(3-glycidoxipropil) trimethoxisilane] solution with 2.5% ethanol anhydride for three hours, at ambient temperature and with orbital agitation. After this time had passed, the devices were washed in ethanol and dried in nitrogen current.

The covalent immobilisation of the antigen on the digits of the electrode was carried out by using 2d-BSA (0.8 μg/ml, 300 μL) antigen solution in carbonate buffered solution (pH=9.6). The reaction was maintained for 24 hours at 25° C. and with orbital agitation. The excess liquid was eliminated by washing the devices with a PBST buffer (four times, 1000 μL/electrode) and drying them in dry nitrogen current.

Biological molecular receptors (antibodies) were designed and produced to analyse antibiotics from the family of sulfamides. The preparation of the biological receptors was approached by means of the design of immunization haptens using molecular modelling strategies. As a consequence of these studies, the synthesis of 2 haptens or antigens was proposed. One of them (hapten 1) kept the greater part of the structure of the sulfamides, while the second (hapten 2) was only a fragment which conserved the part common to most of the compounds of this family of antibiotics. The two haptens were combined to the HCH (horseshoe crab hemocyanin) protein and to the BSA (bovine serum albumin) protein by using methods described in the literature. The covalent bonding of the haptens or antigens and the quantification of the number of the remainder of antigens bonded to the protein was carried out by means of a mass spectrometer. Following this, rabbits of the New Zealand variety were immunised with these antigens by applying a six-month long immunisation protocol, during which the progress of the immune response was controlled by means of extracting small blood samples.

With the aim of evaluating the avidity of the antiserums produced by the sulphonamide-type antibiotics, it was necessary to establish a competitive-type immunochemical assay. To do this, the preparation of 8 competition haptens (SA 3-10) was proposed. These are structures which are chemically similar to the haptens or antigens used to produce the antibodies, but with some structural modifications or with the spacer arm situated at a different point of the molecule. Initially, these haptens have been used to prepare enzymatic tracers with the enzyme HRP (horseradish peroxidise). Preliminary studies with these tracers in direct ELISA format indicated that some antibiotics such as sulfapyrazine could be recognized with an IC50 close to 9 μg L-1.

Sulfapyridine pattern solutions prepared in PBST (0.64 nM-50000 nM, in PBST) were added to the electrodes (150 μL/electrode), followed by a solution with the specific sulfamide antiserum (#155) obtained (1/2000 in PBST, 150 μL/electrode). After incubating for 30 minutes, at ambient temperature, the devices were washed with PBST (three times, 1000 μL/electrode), and once with Mill-Q water (1000 μL/electrode). The reaction was measured in a low conductivity solution. The calibration curves were adjusted to an equation with four parameters, according to the formula: $Y=\{(A-B)/[1+(x/C)^D]\}+B$, where A is the maximum absorbance, B is the minimum absorbance, C is the concentration which produces an absorbance equal to 50% of the maximum and D is the slope at the inflection point of the sigmoid curve.

TABLE 1

Characteristics of the calibration with sulfapyridine[a].

| Assay | [Ab] | [AT, μg/ml] | Max. | Min | Max/min | $IC_{50}$ nM | Slope | $R^2$ |
|---|---|---|---|---|---|---|---|---|
| Sensor | 1/2000 | 0.8 | 19488 | 1038 | 18.8 | 14.01 | −0.82 | 0.99 |
| ELISA | 1/8000 | 0.625 | 0.79 | 0.06 | 13.2 | 9.29 | −0.82 | 0.99 |

[a]These values were obtained from the equation, with four parameters, used to adjust the calibration curve.

The data which is shown in Table 1 represents the parameters characteristic of the immunoenzymatic assay ELISA and of the impedimetric immunosensor. The IC50 indicated the sensitivity, when the most sensitive value of the assay is the smallest. Upon comparing the values of the IC50 of the immunosensor and the ELISA, it was confirmed that they are from the same nature of magnitude, and therefore the immunosensor of the invention behaved similarly to the ELISA assay as regards sensitivity. Another important parameter was the relationship between the maximum signal and the minimum signal, when the value is higher, the better the response of the device of the invention. Going back to comparing the immunosensor of the invention with the ELISA assay confirmed that there had been a better response from the immunosensor with respect to the ELISA. Finally, as an important piece of information, the R2 is presented, which indicates the degree of adjustment of the experimental data to the previously mentioned sigmoid curve, which ended up being identical.

Example 3

Use of the Sensor of the Invention as DNA Biosensor

Before proceeding to the functionalization, the electrodes were cleaned in a solution of 70% absolute ethanol and 30% Milli-Q water. Afterwards, the devices were submerged in a solution of 2.5% NaOH and Milli-Q water for 10 minutes, followed by a rinsing in 100 mL of Milli-Q water, in order to neutralize the action of the NaOH. Finally, the electrodes were cleaned in ethanol and dried in nitrogen current.

The electrodes were introduced into a GPTS [(3-glycidoxipropil) trimethoxisilane] solution with 2.5% ethanol anhydride for three hours, at ambient temperature and with orbital agitation. After this time had passed, the devices were washed in ethanol and dried in nitrogen current.

A single oligonucleotide chain of 20 pairs of bases was immobilised to the surface of the electrodes, with amine groups in position 5'. The devices were submerged in a solution containing an oligonucleotide of 20 pairs of bases (10 μg/ml, 300 μL) in a carbonate buffer (pH=9.6). After 24 hours of reaction time had passed, the electrodes were washed with a PBST buffer (four times, 1000 μL/electrode) and dried in a dry nitrogen current. The oligos were 20 below: 5'-aminohexyl-CGA GTC ATT GAG TCA TCG AG-3'; and 20 above: 5'-fluoresceinahexyl. CTC GAT GAC TCA ATG ACT CG-3'.

The hybridisation of the oligonucleotide was performed, in a buffer solution, with the complementary 20-base pair oligonucleotide, marked with fluorescein in position 5'. The electrodes were introduced in a solution containing the complementary oligonucleotide (10 μg/ml, 300 μL) and incubated for five minutes at ambient temperature. After this time, the devices were washed with a PBST buffer (1000 μL/electrode) and dried in dry nitrogen current. The determination of the hybridisation process was measured in a low conductivity solution.

TABLE 2

Parameters of the oligonucleotides.

| Oligo | 20 initial | 20 complementary |
|---|---|---|
| Length | 20 | 20 |
| GC (content, %) | 50 | 50 |
| Tm (50 mNa, ° C.) | 52.6 | 52.6 |
| Molecular Weight | 6157 | 6157 |
| Ext. Coefficient | 198800 | 188400 |
| mmol/OD 260 | 5.03 | 5.31 |
| μg/ml | 30.97 | 32.26 |

TABLE 3

Figure 3:
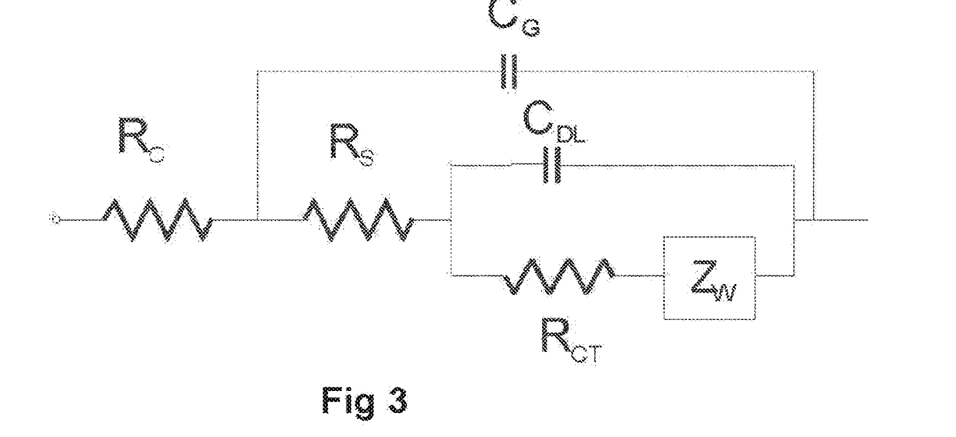

Values obtained for the equivalent circuit elements of FIG. 3, adjusted by means of the commercial programme: Zplot/Zview (Scribner Associates Inc.).

| Device | Rs | Rct |
|---|---|---|
| Free | 118000 | 3541 |
| Funcionalized | 29645 | 2645 |
| With Oligonucleotide | 50538 | 1889 |
| Hybridised | 43528 | 10014 |

In this table 3, the values of two parameters obtained from the adjustment of the experimental impedance measure data are shown by means of the commercial programme: Zplot/Zview (Scribner Associates Inc.). As can be observed in the represented values, Rs and Rct, there was a significant change between the sensor device of the invention with the initial immobilised oligonucleotide chain on the surface and the same device with the hybridised oligonucleotide chain with its complementary. This observed difference indicated that the sensor of the invention can be used to distinguish the hybridisation of oligonucleotide chains.

The invention claimed is:

1. An impedimetric biosensor for directly determining the presence of analytes in a sample characterised in that it comprises:
   i) an insulating substrate or non-insulating substrate covered with an insulating layer,
   ii) at least, a pair of chemically inert interdigitated electrodes and formed with a highly electrically conductive material, disposed on the substrate and each pair of digits separated, but not covered, by
   iii) a barrier made of an insulating material into which welding points open for external wire connection to each of the electrodes, wherein the insulating barrier comprises a thickness of the insulating layer which defines the height of the barrier separating two adjacent digits, the thickness comprising from 50% to 150% of the distance separating the centres of the pair of consecutive interdigitated electrodes, and
   iv) chemically immobilised receptor molecules on the surface of the insulating material of the barriers.

2. The biosensor according to claim 1, wherein the receptor molecule comprises enzymes, antibodies, antigens, peptides, DNA fragments, RNA fragments or oligonucleotides.

3. The biosensor according to claim 1, wherein the substrate from i) is of a material belonging to the following group: a polymer, a glass or an inorganic oxide.

4. The biosensor according to claim 1, wherein the substrate from i) is not of an insulating material but comprises an insulating or dielectric layer of a material belonging to: silicon dioxide or a polymer.

5. The biosensor according to claim 1, wherein the highly conductive and inert electrodes from ii) are of a material selected from the group consisting of metals, oxides, Si, silicon polycrystalline, tantalum silicide and polymer conductors.

6. The biosensor according to claim 1, wherein the electrodes have digits with a width and a separation between each pair of digitated electrodes, the width and separation individually comprising from 0.5 to 10.0 μm.

7. The biosensor according to claim 1, wherein the insulating barrier from iii) is of a material selected from the group consisting of inorganic oxides, polymers and materials sensitive to the exposure of UV light.

8. The biosensor according to claim 1, wherein the receptor molecules are immobilised on a surface of the electrodes.

9. The biosensor according to claim 1, wherein the electrodes are organized according to an interdigitated array.

10. The biosensor according to claim 1, further comprising a device or an apparatus which detects the electrical properties connected to the electrodes from ii) whereto is applied an AC voltage, and which detects the variation in the electrical field close to the surface of the barriers, and a device or apparatus to apply said voltage.

11. The biosensor according to claim 10, wherein the detection device is an impedimeter which measures the impedance between the electrodes of the sensor.

12. The biosensor according to claim 1, further comprising a plurality of sensing biomolecules including more than one type of biomolecule or a plurality of biomolecules comprising biomolecules of the same type directed to different target molecules.

13. A method for analyzing a biological sample, comprising
adding a solution to be tested to a biosensor according to claim 1 or submerging the biosensor in a biological sample; and
measuring AC impedance of the solution or biological sample with the biosensor.

14. The biosensor according to claim 5, wherein the highly conductive and inert electrodes comprise Pt, Pd or Au.

15. The biosensor according to claim 1, wherein the insulating barrier iii) comprises a thickness of about 100% of the distance separating the centres of the pair of consecutive interdigitated electrodes.

16. The biosensor according to claim 12, wherein the biomolecules comprise nucleic acids, antigens, antibodies, enzymes, proteins, or peptides.

* * * * *